United States Patent [19]

Tsuji et al.

[11] Patent Number: 4,705,669

[45] Date of Patent: Nov. 10, 1987

[54] GAS ANALYZER FOR SIMULTANEOUSLY MEASURING MANY INGREDIENTS

[75] Inventors: Katsuya Tsuji; Masahiro Tanimoto; Akihiro Hirano; Takeshi Yamada, all of Kyoto, Japan

[73] Assignee: Horiba, Ltd., Kyoto, Japan

[21] Appl. No.: 901,046

[22] Filed: Aug. 27, 1986

[30] Foreign Application Priority Data

Oct. 19, 1985 [JP] Japan .................................. 60-235943

[51] Int. Cl.$^4$ .......................................... G01N 35/08
[52] U.S. Cl. .................................. 422/93; 422/82; 422/83; 422/306; 436/52; 436/53; 137/599.1; 137/606
[58] Field of Search ............ 422/82, 83, 93, 306; 436/53, 106, 127, 136, 158, 52; 73/863.31, 863.33, 863.72, 863.73, 864.83, 864.84; 137/599.1, 606

[56] References Cited

U.S. PATENT DOCUMENTS

| | | | |
|---|---|---|---|
| 3,080,760 | 3/1963 | Piersma | 73/863.31 |
| 3,690,833 | 9/1972 | Ferrari | 422/82 |
| 3,830,256 | 8/1974 | Cox | 137/606 |
| 3,886,971 | 6/1975 | Lundsgaard | 137/606 |
| 3,997,297 | 12/1976 | Jenkins et al. | 422/93 |
| 4,498,496 | 2/1985 | Barcellona et al. | 137/599 |

OTHER PUBLICATIONS

Electronic Sequencing for Multiport Valves Electronic Engineering (GB), vol. 49, No. 589, p. 21, Mar. 1977.

*Primary Examiner*—S. Leon Bashore
*Assistant Examiner*—Lori-Ann Cody
*Attorney, Agent, or Firm*—Wenderoth, Lind & Ponack

[57] ABSTRACT

A gas analyzer for simultaneously measuring a plurality of ingredients of a sample gas has a sample gas-introducing passage, a sample gas, flow-divider connected to the gas-introducing passage for dividing the sample gas into a plurality of gas flows in a desired flow-dividing ratio, a sample gas-diluter connected to the flow-divider for diluting the plurality of divided sample gas flows, and a plurality of gas concentration detectors, one for each gas flow, and connected in parallel with each other to said sample gas-diluter for receiving the respective diluted gas flows from the sample gas-diluter.

1 Claim, 9 Drawing Figures

GAS ANALYZER FOR SIMULTANEOUSLY MEASURING MANY INGREDIENTS

BACKGROUND OF THE INVENTION

1. Field of the Invention

The present invention relates to a gas analyzer for simultaneously measuring many ingredients in a gas and which is adapted to be able to simultaneously measure at least two kinds of ingredient gases contained in a sample gas. In particular it provides a novel gas analyzer for simultaneously measuring many ingredients which can meet the requirement of simultaneous and high accuracy measurement of the concentration of a high-concentration ingredient gas and that of a low-concentration ingredient gas in a sample gas comprising a mixture of the high-concentration ingredient gas and the low-concentration ingredient gas. Such a gas analyzer has heretofore been considered difficult to achieve.

2. Description of the Prior Art

A gas extraction type metal analyzer for measuring the quantity of various kinds of impurities contained in a metallic sample and the like has been known, and is a gas analyzer which can simultaneously measure many ingredients and in so doing can simultaneously measure at least two kinds of ingredient gas.

This gas extraction type metal analyzer is, as shown in FIG. 6, comprised of a gas extraction portion 0A and a gas analyzer portion 0B connected to said gas extraction portion 0A for simultaneously measuring a plurality of ingredients, e.q. two ingredients. Said gas extraction portion 0A is comprised of a heating furnace 01, for example a graphite crucible, for driving off various kinds of ingredient gas, such as CO gas, $N_2$ gas, $H_2$ gas and the like, corresponding to various kinds of impurities such as oxygen, nitrogen, hydrogen and the like, contained in the metallic sample by heating the metal sample to melt it in the presence of a carrier gas, e.q. an inert gas such as He gas, fed through a carrier gas-introducing passage 00. An electro-magnetic purge valve 02 is connected to the outlet of the furnace. Said gas analyzer portion 0B for simultaneously measuring a plurality of ingredients, in this embodiment two ingredients, is comprised of a pressure regulator 04, a flow control needle valve 05, a first gas concentration detector $0D_1$ for measuring the concentration of CO gas, which can be, a non-dispersion type infrared detector, an oxidizer 06 for oxidizing CO gas and $H_2$ gas contained in the sample gas which has passed through said first gas concentration detector $0D_1$, to turn the CO gas to $CO_2$ gas and the $H_2$ gas to $H_2O$ gas, respectively, a $CO_2$-remover 07 for removing $CO_2$ gas by a chemical reaction between it and a $CO_2$-removing agent, a $H_2O$-remover 08 for removing $H_2O$ gas by a $H_2O$-adsorbent, a second gas concentration detector $0D_2$ for measuring the concentration of $N_2$ gas in the sample gas, which detector can be a heat conductivity type detector, and an exhaust passage 09 connected in series in the recited order. The gas analyzer portion 0B is connected to the gas extraction portion 0A through a sample gas-introducing passage 03, which is connected with said electro-magnetic purge valve 02 of said gas extraction portion 0A. However, such gas analyzer portion for simultaneously measuring a plurality of ingredients having the conventional construction used in the above described gas extraction type metal analyzer has shown the following various disadvantages. With the conventional gas analyzer, for simultaneously measuring a plurality of ingredients, since the measurable upper limit is at most several thousands ppm, only small quantities of various kinds of impurities contained in the metallic sample can be accurately measured. Also, even where a comparatively large amount of various kinds of substances are contained in the sample, if these various kinds of substances are not present in greatly differing quantities, the gas analyzer can in practice be used without any problem only by suitably diluting the sample gas obtained from the sample.

However, recently it has became increasingly important to be able to simultaneously analyze ceramics and the like for many ingredients, such as the principal ingredients and impurities, such as $Si_3N_4$ having a large amount, such as of several tens %, of nitrogen as a principal ingredient, and a very small amount, such as only several %, of oxygen as an impurity, and $Fe_2O_3$ having a large amount, such as several tens %, of oxygen as a principal ingredient, and a very small amount of nitrogen as an impurity. To date there is no analyzer meeting such a requirement, so that to make such an analysis it has been necessary to use the above described gas analyzer having a conventional construction for simultaneously measuring the ingredients.

In such a case it is necessary in order to measure the high-concentration ingredient gas corresponding to the principal ingredients to sample a very small size sample, for example 1 to 2 mg or to greatly dilute the sample gas obtained from a suitable amount of sample material. Accordingly, problems have occurred in that errors of measurement in the measurement of the weight of the sample are relatively increased and influence of the segregations within the sample is inevitable, so that the analytical accuracy is reduced. Further, since the concentration of the ingredient gas corresponding to the impurities is very low, the accuracy of the measurement of the impurities is greatly reduced.

Moreover, with the conventional gas analyzer for simultaneously measuring many ingredients, the problem has occurred in that since the first gas concentration detector $0D_1$ and the second gas concentration detector $0D_2$ are arranged in series, fundamentally speaking, errors of measurement due to an increase of sensitivity resulting from back pressure from gas concentration detector $0D_2$ are liable to appear in the first gas concentration detector $0D_1$. Also the problem has occurred that in particular, as shown in said FIG. 6, in the case where a heat conductivity type detector having no selectivity for the gas being analyzed is used as the second gas concentration detector $0D_2$, it is necessary to provide to oxidizer 06, the $CO_2$-remover 07, the $H_2O$-remover 08 and the like between the first gas concentration detector $0D_1$ and the second has concentation detector $0D_2$, so that the influence of the back pressure upon the first gas concentration detector $0D_1$ is gradually increased principally due to progressive clogging of the $CO_2$-remover 07 with the passage of time, whereby errors of measurement due to an increase of sensitvity in the first gas concentration detector $0D_1$ are increased with the passage of time.

SUMMARY OF THE INVENTION

The present invention was made after taking the above described problems into consideration, and it is an object of the present invention to provide a gas analyzer for simultaneously measuring many ingredients, which apparatus can be widely used for the simultaneous and highly accurate measurement of the concentration of each ingredient gas contained in a sample gas which is a mixture of a high-concentration ingredient gas and a low-concentration ingredient gas, in for example, the analysis of ceramics, and can carry out not only the simultaneous analysis of impurities in the sample but also the simultaneous analysis of the principal ingredients and impurities, and which has a construction in which each gas concentration detector is hardly influenced at all by the presence of another gas concentration detector in the analyzer.

In order to achieve the above described object, the gas analyzer for simultaneously measuring many ingredients according to the present invention comprises, a plurality of gas concentration detectors connected with a sample gas-introducing passage so that at least two ingredient gases contained in a sample gas fed through the sample gas-introducing passage can be simultaneously measured, said plurality of gas concentration detectors being connected in parallel to said sample gas-introducing passage, said sample gas-introducing passage being provided with sample gas flow-dividing means which can divided the sample gas in a desired ratio to feed the respective gas concentration detectors with the respective flows into which the sample gas has been divided, and sample gas-diluting means for further diluting the sample gas divided by said sample gas-dividing means and provided between said sample gas-dividing means and said gas concentration detectors. In addition, an appropriate oxidizer, $CO_2$-gas remover, and $H_2O$-remover can be provided.

In the gas analyzer according to the present invention, the sample gas flow is divided in a desired ratio, and the parts of the divided flow of the sample gas are further diluted, and then supplied to respective gas concentration detectors connected in parallel to the sample gas-introducing passage, so that the respective sample gas flows supplied to the gas concentration detectors corresponding to ingredient gases to be detected can be diluted to a concentration suitable for the measurement thereof by suitably setting the flow-dividing ratio of the sample gas-dividing means and the dilution ratio of each sample gas-diluting means. Even in the case where a sample gas mixture comprises a high-concentration ingredient gas and a low-concentration ingredient gas, such as are produced in the analysis of ceramics, both the high-concentration principal ingredient gas and the low-concentration impurity gas can be simultaneously measured with very high accuracy. In addition, it is unnecessary to greatly reduce the quantity of the sample, so that the sampling method can be simplified. In addition, the analytical accuracy can be greatly improved due to the improvement of the sampling accuracy and the reduction of the influence of the segregations within the sample. Also in the case where all ingredient gases have a low concentration, such as in the analysis of impurities in metals or in the case where all ingredient gases have a high concentration, each of the sample gas flows supplied to the gas concentration detectors corresponding to ingredient gases can be diluted to a concentration suitable for the measurement thereof by suitably setting the flow-dividing ratio of the sample gas-dividing means and the diluting ratio of each sample gas-diluting means similarly to the manner described above, so that a highly accurate simultaneous analysis is possible. Furthermore, since a plurality of gas concentration detectors are connected in parallel to the sample gas-introducing passage, other gas concentration detectors need not be provided in the lower reach of each gas concentration detector. Also in the case where a heat conductivity type detector or the like having no selectivity with respect to the gas being detected is used as one of the plurality of gas concentration detectors and it is necessary to provide an oxidizer, a $CO_2$-remover, a $H_2O$-remover and the like, it is sufficient to provide them only in the upper reaches of the heat conductivity type gas concentration detector, so that errors of measurement due to the influence of the back pressure incidental to the conventional gas concentration detector do not occur in any one of the gas concentration detectors. This achieves a remarkable improvement of the synthetic analytical accuracy. All in all, with a gas analyzer for simultaneously measuring many ingredients according to the present invention, a superior effect can be obtained in that many ingredient gases contained in a wide range of sample gas having various kinds of ingredient gas concentration distribution can be simultaneously measured, and always with high accuracy.

DESCRIPTION OF THE PREFERRED EMB0DIMENTS

Figure 1:
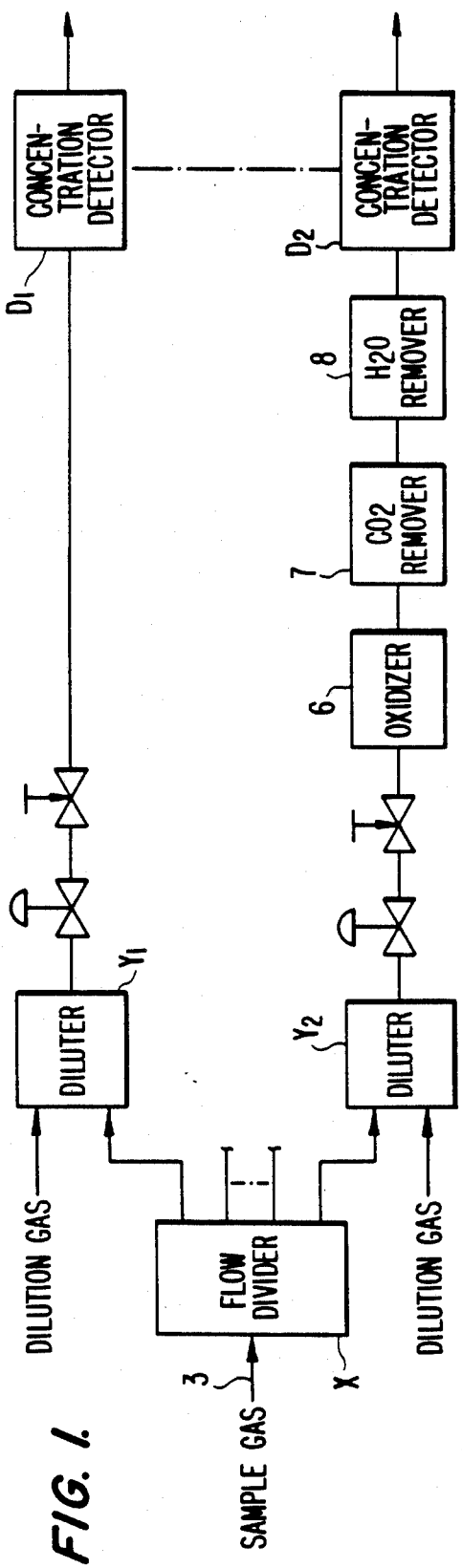
FIG. 1 is a schematic diagram showing the fundamental construction of a gas analyzer for simultaneously measuring many ingredients according to the present invention.
Figure 6:
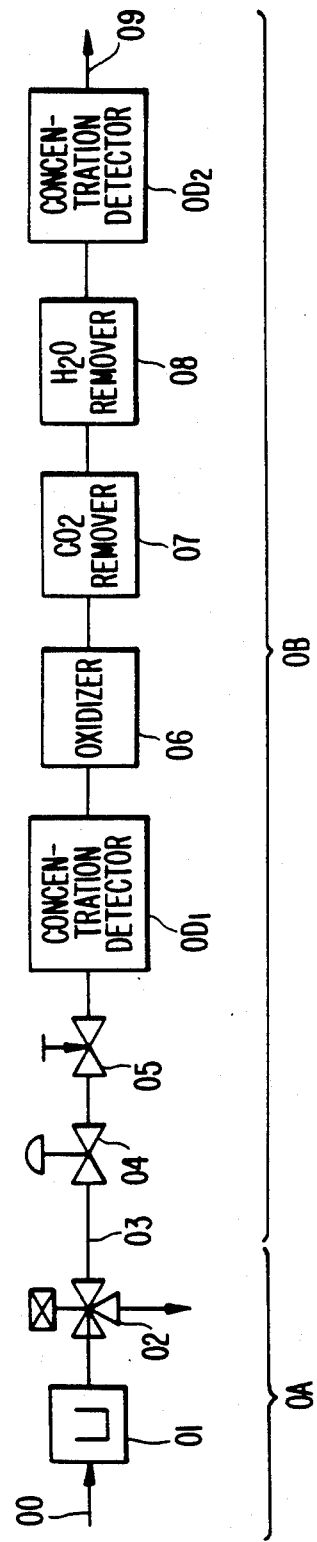
FIG. 6 is a general diagram showing a conventional gas extraction type metal analyzer in which a gas analyzer for simultaneously measuring two ingredients is used.

As shown in FIG. 1, the gas analyzer according to the present invention for simultaneously analyzing a sample gas to measure many ingredients therein comprises a plurality of gas concentration detectors $D_1$ and $D_2$ connected in parallel to the sample gas introducing passage 3 so that at least two ingredient gases contained in the sample gas fed through the sample gas introducing passage 3 can be simultaneously measured. The sample gas introducing passage 3 is provided with a sample gas flow-dividing means X which can divide the sample gas in a desired ratio to feed the respective gas concentration detectors $D_1$ and $D_2$ with the respective flows into which the sample gas has been divided. Sample gas diluting means $Y_1$ and $Y_2$ for further diluting the sample gas divided by the sample gas dividing means is provided between the sample gas dividing means X and the gas concentration detectors $D_1$ and $D_2$. In addition, an appropriate oxidizer 6, $CO_2$ gas remover 7, and $H_2O$ remover 8 can be provided upstream of one of the gas concentration detectors, here the gas concentration detector $D_2$.

In this gas analyzer, the sample gas flow is divided into flows in the desired ratio in the dividing means X, and the respective flows are further diluted in the diluting means $Y_1$ and $Y_2$ and then supplied to the respective gas concentration detectors $D_1$ and $D_2$.

The respective gas flows to be diluted to a concentration suitable for the measurement of the ingredients thereof by choosing a suitable flow dividing ratio and a suitable dilution ratio for the respective flows.

The preferred embodiments of the present invention will be described with reference to FIGS. 2 to 5.

Figure 2:
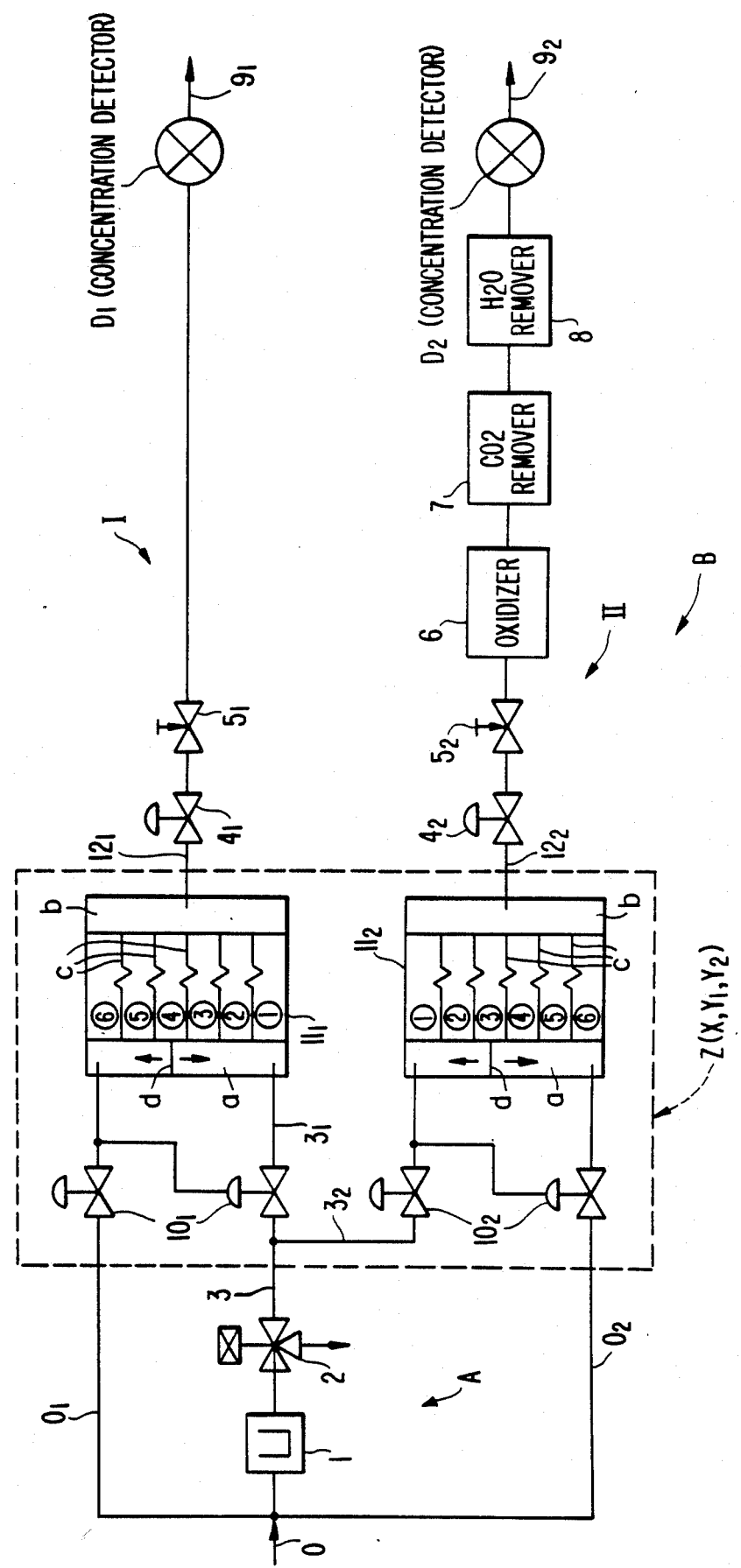
FIG. 2 is a somewhat more detailed diagram of a preferred embodiment of the present invention.

FIG. 2 shows a gas extraction type sample analyzer in which a gas analyzer for simultaneously measuring many ingredients according to the present invention is used.

This gas extraction type sample analyzer comprises, as shown in FIG. 2, a gas extraction portion A and a gas-analyzing portion B connected with said gas extraction portion A for simultaneously measuring two ingredients.

Said gas extraction portion A comprises a heating furnace 1 for example a graphite crucible, for heating a sample material to drive off various kinds of ingredient gas, for example CO gas, $N_2$ gas, $H_2$ gas and the like, corresponding to various kinds of ingredients, in this embodiment oxygen, nitrogen, hydrogen and the like, contained in a sample of ceramics, metals or the like. The heating takes place in the presence of a carrier gas, for example, an inert gas such as He gas, supplied from a carrier gas-introducing passage 0. An electro-magnetic purge valve 2 is connected downstream of the furnace 1.

The gas-analyzing portion B comprises a CO concentration-measuring system I and a $N_2$ concentration-measuring system II connected in parallel to a sample gas-introducing passage 3 connected with said electro-magnetic purge valve 2 of said gas extraction portion A.

Said CO concentration-measuring system I comprises a first sample gas branch passage $3_1$ branched from said sample gas-introducing passage 3, a first carrier gas passage $0_1$ branched from said carrier gas-introducing passage 0, a first pressure-regulating governor $10_1$ connected between said first sample gas branch passage $3_1$ and said first carrier gas passage $0_1$, a first flow-dividing ratio/diluting ratio-setting device $11_1$ to which said first sample gas branch passage $3_1$ and said first carrier gas passage $0_1$ are connected, a first pressure regulator 4, a first flow rate-adjusting needle valve 5 a first gas concentration detector $D_1$, comprising a non-dispersion type infrared detector for use in the measurement of the concentration of CO gas provided in a first exit passage $12_1$ from said first flow-dividing ratio/diluting ratio-setting device 11, and a first exhaust passage $9_1$. In addition, said $N_2$-measuring system II comprises a second sample gas branch passage $3_2$ branched from said sample gas-introducing passage 3, a second carrier gas passage $O_2$ branched from said carrier gas-introducing passage 0, a second pressure-regulating governor $10_2$ laid between said second sample gas passage $3_2$ and said second carrier gas passage $0_3$, a second flow-dividing ratio/diluting ratio-setting device $11_2$ with which said second sample gas branch passage $3_2$ and said second carrier gas passage $0_2$ are connected, a second pressure regulator $4_2$, a second flow rate-adjusting needle valve $5_2$, an oxidizer 6 for oxidizing CO gas and $H_2$ gas contained in the sample gas, to turn to $CO_2$ gas and $H_2O$ gas, a $CO_2$-remover 7 for removing the resulting $CO_2$ gas by the chemical reaction between it and a $CO_2$-removing agent, an $H_2O$-remover 8 for removing the resulting $H_2O$ gas by an $H_2O$ adsorbent, a second gas concentration detector $D_2$ comprising a heat conductivity type detector for use in the measurement of the concentration of $N_2$ gas and provided in a second exit passage $12_2$ from said second flow-dividing ratio/diluting ratio-setting device $11_2$, and a second exhaust passage $9_2$.

The portion encircled by a dotted line in FIG. 2 mainly comprising said first flow-dividing ratio/diluting ratio-setting device $11_1$ and said second flow-dividing ratio/diluting ratio-setting device $11_2$ constitutes a sample gas flow-dividing/diluting means Z which can be used both as sample gas flow-dividing means X and sample gas-diluting means $Y_1$, $Y_2$ described in connection with FIG. 1. Said sample gas flow-dividing/diluting means Z is adapted to divide the flow of the sample gas supplied through said sample gas-introducing passage 3 at a desired ratio, dilute the divided sample gas, and supply the first gas concentration detector $D_1$ and the second gas concentration detector $D_2$ connected in parallel to said sample gas-introducing passage 3 with the respective flows of diluted sample gas. In other words, said sample gas-diluting means $Y_1$, $Y_2$ is constructed from said flow-dividing ratio/diluting ratio-setting means $11_1$, $11_2$, respectively, so as to also function as said sample gas flow-dividing means X.

Each of said flow-dividing ratio/diluting ratio-setting means $11_1$, $11_2$ comprises an inlet space a connected with the corresponding sample gas branch passage $3_1$ or $3_2$ at one end thereof and connected with the corresponding carrier gas passage 0, or $0_2$ at the other end thereof, an outlet space b from which the corresponding exit passage $12_1$ or $12_2$ extends, a plurality (5 in this embodiment) of flow rate limiting elements, for example capillaries C, communicating said inlet space a with said outlet space b, and each limiting the flow therethrough to a predetermined amount, preferably an amount equal to the flows through the other elements, and a valve body d dividing said inlet space a into a part with which the sample gas branch passage $3_1$ or $3_2$ is connected and a space with which said carrier gas passage $0_1$ or $0_2$ is connected. Said plurality of flow rate elements c used in this embodiment all have the same flow rate characteristics. In addition, the carrier gas, such as He gas, introduced through said carrier gas passage $0_1$ or $0_2$ is used as a diluting gas in said flow-dividing ratio/diluting ratio-setting devices $11_1$ and $11_2$. Said valve body d in said inlet space a is adapted to be positioned at an optional position corresponding to ①, ②, ③, ④, ⑤, ⑥ in the drawing. Thus, each of said flow-dividing ratio/diluting ratio-setting devices $11_1$ and $11_2$ can optionally adjust the flow-dividing ratio of the sample gas for each of said measuring systems I, II as well as the diluting ratio of the divided sample gas by the optional setting of the position of said valve body d. In addition, when the flow-dividing ratio is set to be large in each of said flow-dividing ratio/diluting ratio-setting devices $11_1$ and $11_2$, the diluting ratio is automatically set to be small, so that accordingly the total dilution is small, while when the flow-dividing ratio is set to be small, the diluting ratio is automatically set to be large and accordingly, the total dilution is large. For example, under the condition as shown in FIG. 2, since the valve body d of the first flow-dividing ratio/diluting ratio-setting device $11_1$ is positioned at the position ④, an amount of the sample gas corresponding to the amount flowing through three flow rate elements c, and a carrier gas of a quantity corresponding to the amount flowing through two flow rate elements c, are introduced into the outlet space b of the first flow-dividing ratio/diluting ratio-setting device $11_2$ while since the valve body d of the second flow-dividing ratio/diluting ratio-setting device $11_2$ is positioned at the position ③, the amount of sample gas corresponding to the amount flowing through two flow rate elements and carrier gas in a quantity corresponding to the amount flowing through three flow rate elements c, are introduced into the outlet space b of the second flow-dividing ratio/diluting ratio-setting device $11_2$. Accordingly, the sample gas introduced through said sample gas-introducing passage 3 is transferred to the flow-dividing ratio/diluting ratio-setting devices $11_1$, $11_2$ at a flow-dividing ratio of 3 : 2 and the sample gas transferred to the first flow-dividing ratio/diluting ratio-setting device $11_1$ is diluted at a diluting ratio of 3/5 preparatory to being introduced into the measuring system I, while the sample gas transferred to the second flow-dividing ratio/diluting ratio-setting device $11_2$ is diluted at a diluting ratio of 2/5 preparatory to being introduced into the measuring system II.

With a gas extraction type sample analyzer constructed in the above described manner, the following wide range of sample gases can be subjected to various kinds of measurement.

Figure 3A:
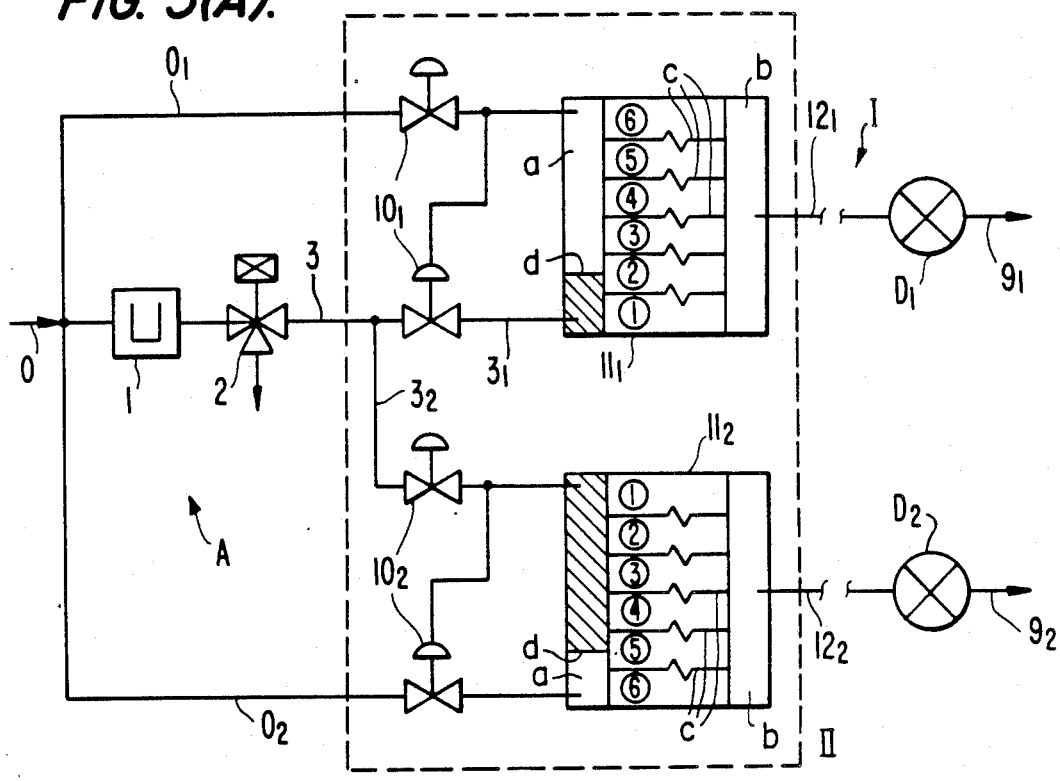
FIG. 3A–3D are diagrams similar to part of FIG. 2 showing the states of certain of the parts of the embodiment of FIG. 2 for explaining various kinds of operations thereof.

For example, in the case where a sample such as an oxide, e.g. $Fe_2O_3$, comprising a large quantity of oxygen as a principal ingredient and a very small quantity of nitrogen as an impurity is analyzed, the valve body d of the first flow-dividing ratio/diluting ratio-setting device $11_1$ is set at, for example, the position ② and the valve body d of the second flow-dividing ratio/diluting ratio-setting device $11_2$ is set at, for example, the position ⑤, as shown in FIG. 3(A), whereby the sample gas introduced through the sample gas-introducing passage 3 is transferred to the first flow-dividing ratio/diluting ratio-setting device $11_1$ and the second flow-dividing ratio/diluting ratio-setting device $11_2$ at a flow-dividing ratio of 1 : 4 and the sample gas transferred to the first flow-dividing ratio/diluting ratio-setting device $11_1$ is diluted at a small diluting ratio of 1/5 while the sample gas transferred to the second flow-dividing ratio/diluting ratio-setting device $11_2$ is diluted at a large diluting ratio of 4/5. Thus the sample gas diluted to a large extent is introduced into the CO concentration-measuring system I for measuring a large quantity of oxygen, which is a principal ingredient, while the sample gas diluted to a small extent is introduced into the $N_2$ concentration-measuring system II for measuring a small quantity of nitrogen, which is an impurity.

Figure 3B:
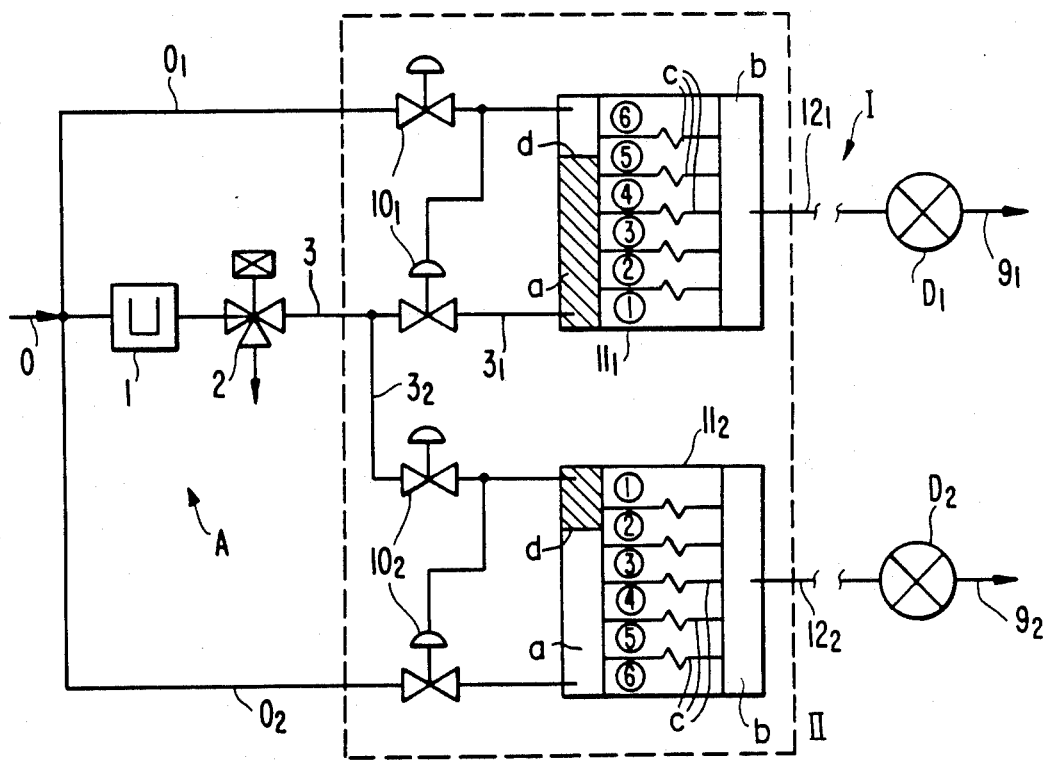

In the case where a sample such as a silicide, e.g. $Si_3N_4$, comprising a large quantity of nitrogen as a principal ingredient and a very small quantity of oxygen as an impurity is analyzed, the valve body d of the first flow-dividing ratio/diluting ratio-setting device $11_1$ is positioned at, for example, the position ⑤ and the valve body d of the second flow-dividing ratio/diluting ratio-setting device $11_2$ is set at, for example, the position ②, as shown in FIG. 3(B), whereby the sample gas introduced through the sample gas-introducing passage 3 is transferred to the flow-dividing ratio/diluting ratio-setting devices $11_1$, $11_2$ at flow-dividing ratio of 4 : 1 and the sample gas transferred to the first flow-dividing ratio/diluting ratio-setting device $11_1$ is diluted at a large diluting ratio of 4/5 while the sample gas transferred to the second flow-dividing ratio/diluting ratio-setting device $11_2$ is diluted at a small diluting ratio of 1/5. Thus the sample gas diluted to a small extent is introduced into the CO concentration-measuring system I for measuring the small quantity of oxygen which is an impurity while the sample gas diluted to a large extent is introduced into the $N_2$ concentration-measuring system II for measuring the large quantity of nitrogen which is a principal ingredient.

Figure 3C:
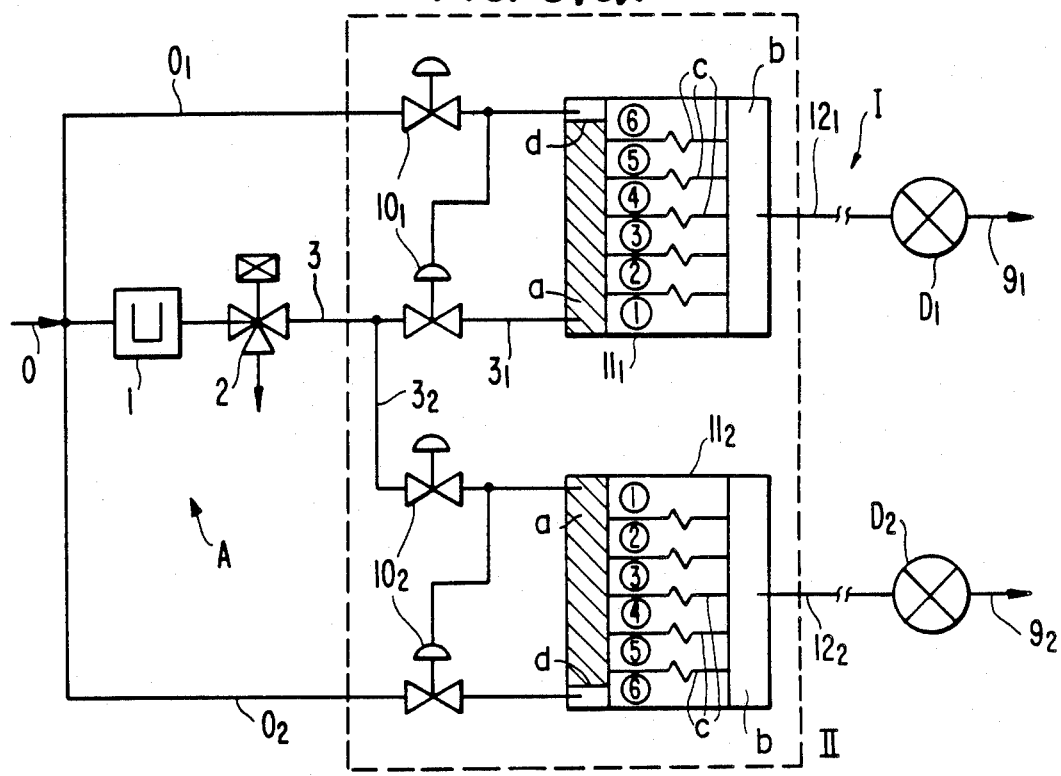

In the case where a sample such as metal, comprising a very small but almost equal quantity of impurities such as oxygen and nitrogen is analyzed, the valve body d of both the first flow-dividing ratio/diluting ratio-setting device $11_1$ and the second flow-dividing ratio/diluting ratio-setting device $11_2$ are positioned at, for example, the position ⑥, as shown in FIG. 3(C), whereby the sample gas introduced through the sample gas-introducing passage 3 is transferred to the flow-dividing ratio/diluting ratio-setting devices $11_1$ and $11_2$ at a flow-dividing ratio of 1 : 1 and both the sample gas transferred to the first flow-dividing ratio/diluting ratio-setting device $11_1$ and the sample gas transferred to the second flow-dividing ratio/diluting ratio-setting device $11_2$ are diluted at a diluting ratio of 0/5, that is to say the sample gas flow is divided but not diluted.

Figure 3D:
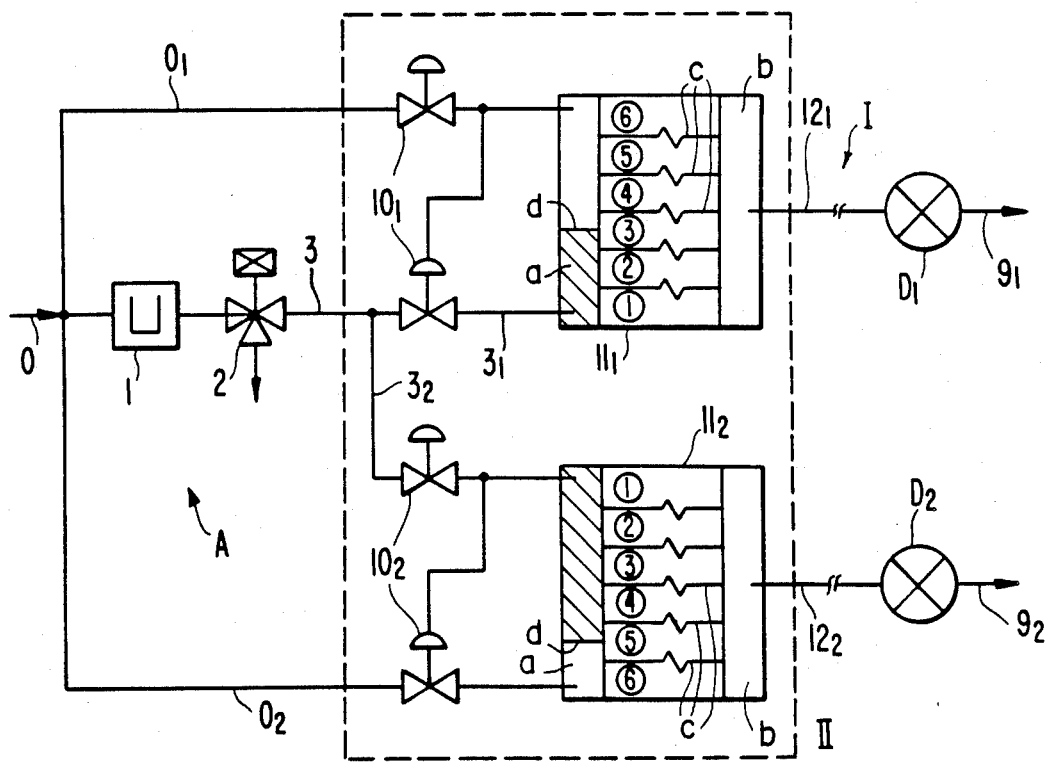

In addition, depending on the sample gas to be measured, the valve body d of the second flow-dividing ratio/diluting ratio-setting device $11_2$ can be optionally positioned at suitable positions, as shown in FIG. 3(D), whereby many ingredients contained in a wide range of samples having various ingredient gas concentration distributions can be simultaneously measured with high accuracy by means of a single apparatus.

Figure 4:
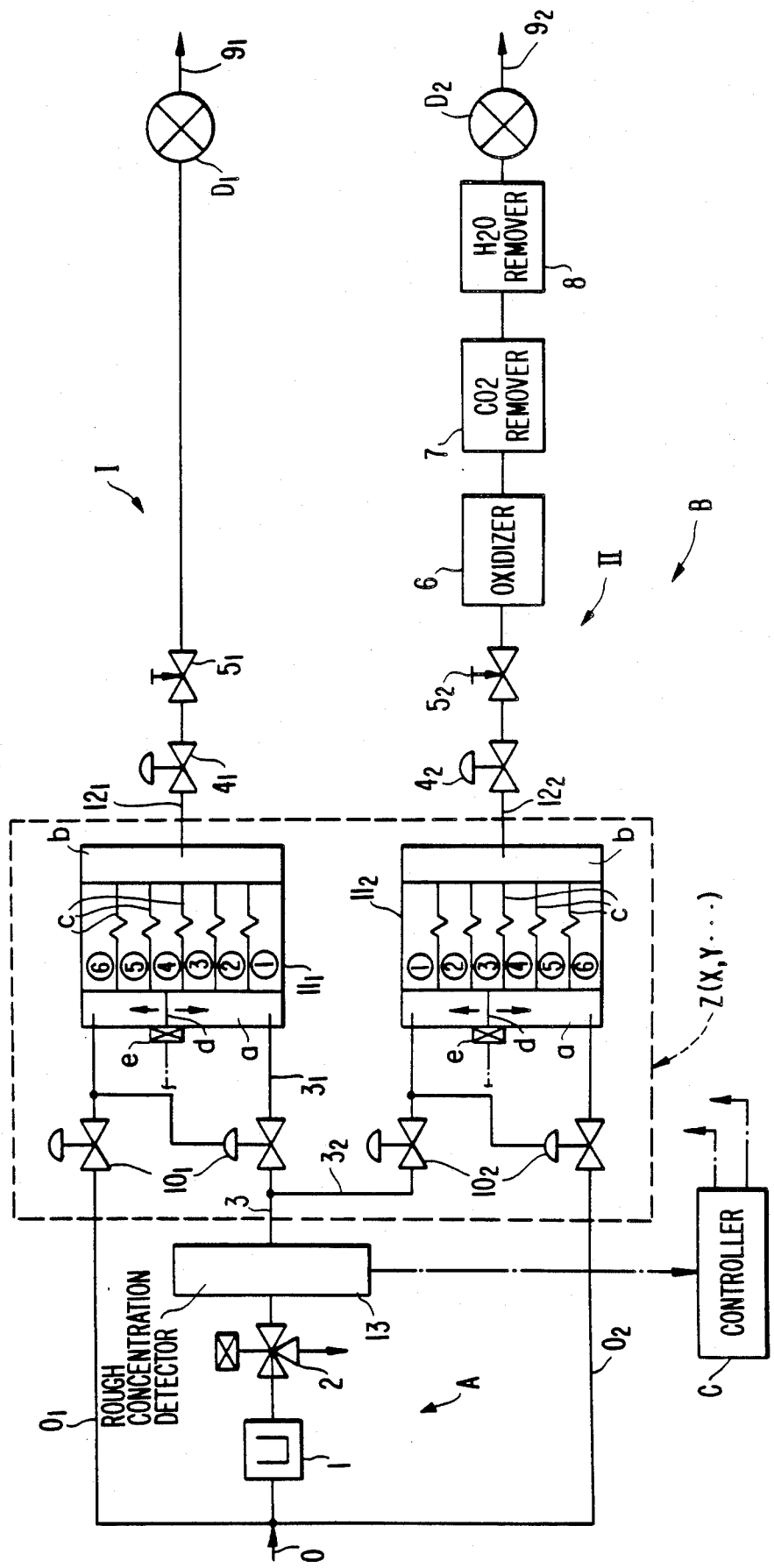
FIG. 4 is a view similar to FIG. 2 showing another preferred embodiment of the present invention.

FIG. 4 shows another preferred embodiment, in which the sample gas-introducing passage 3 is provided with a rough concentration detector 13 for detecting rough concentrations of ingredients contained in a sample gas introduced therein and the valve bodies d of the flow-dividing ratio/diluting ratio-setting devices $11_1$ and $11_2$ are provided with actuating mechanisms e, respectively, whereby the valve body d can be automatically set to be positioned at a suitable position by means of a controller C on the basis of the rough concentration ratio of ingredient gases detected by said rough concentration detector 13. Other members are similar to those in the earlier described embodiment.

Figure 5:
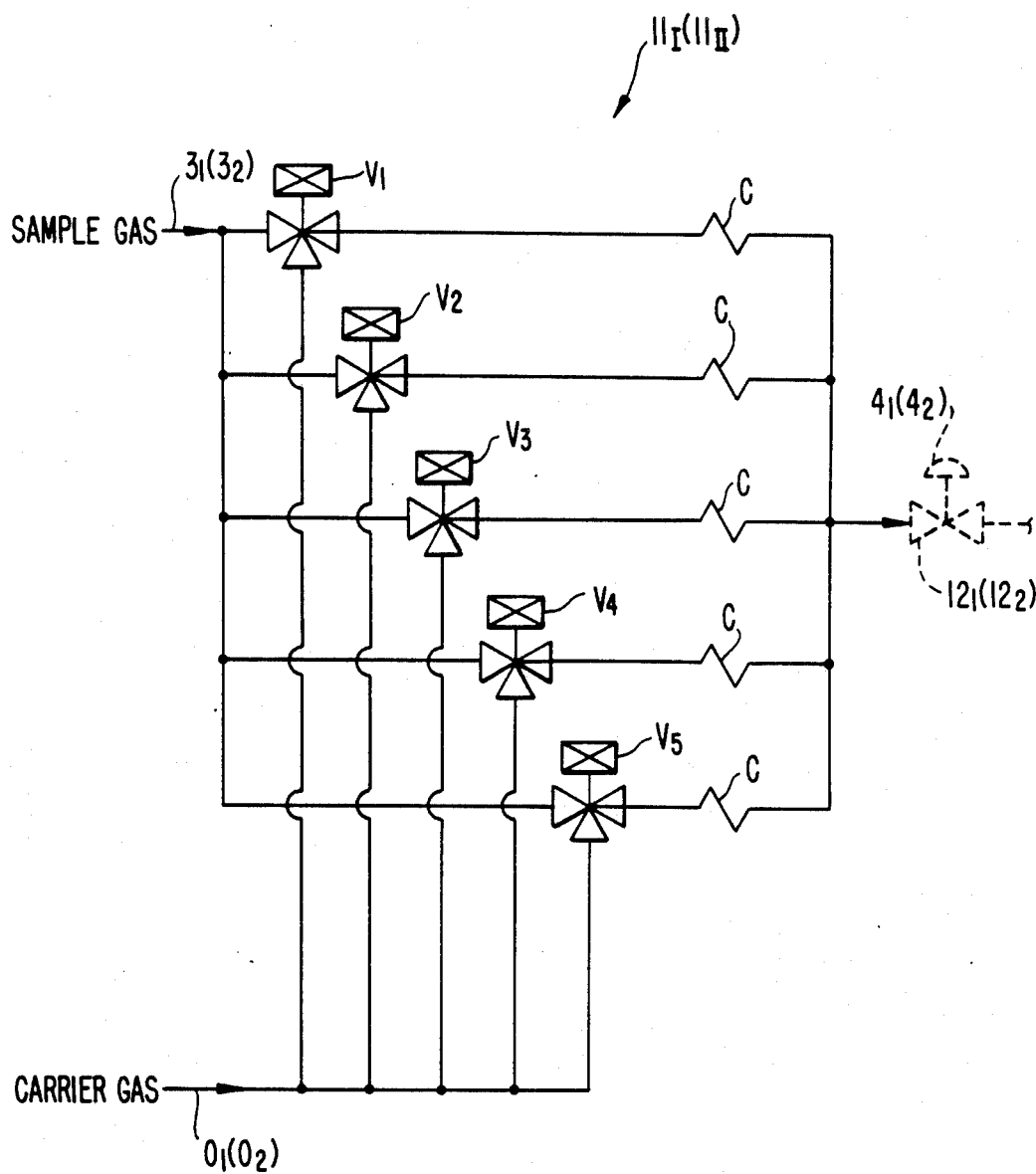
FIG. 5 is a diagram a preferred embodiment of one of the principal members of the apparatus.

FIG. 5 shows another preferred embodiment of the flow-dividing ratio/diluting ratio-setting devices $11_1$ and $11_2$, each comprising a plurality (five in this embodiment) of electromagnetic three-way valves $v_1$, $v_2$ . . . to one of the inlets thereof the branched passage from the sample gas branch passage $3_1$ or $3_2$ is connected and to the other inlet the branch carrier gas passage $0_1$ or $0_2$ are connected, and flow rate elements (for example capillaries) c connected with the outlets of said electromagnetic three-way valves $v_1$, $v_2$ . . . . The flow-dividing ratio/diluting ratio-setting devices $11_1$ and $11_2$ with such a construction carry out the same flow dividing and dilution as do the flow-dividing ratio/diluting ratio-setting devices $11_1$ and $11_2$ of the constructions as described in the earlier described embodiments.

Although a gas analyzer capable of simultaneously measuring two ingredients has been described in the above described embodiments, it is easy to provide a gas analyzer for simultaneously measuring many ingredients, i.e. three or more ingredients by simply connecting further gas flow-dividing/diluting means and concentration detecting systems in parallel.

In addition, although a sample gas flow-dividing/diluting means Z, in which a sample gas flow-dividing means X and sample gas-diluting means $Y_1$ and $Y_2$ are combined, has been described in the above described embodiments, it goes without saying that sample gas flow-dividing means X and sample gas-diluting means $Y_1$, and $Y_2$ may be independently provided.

What is claimed is:

1. A gas analyzer for simultaneously measuring a plurality of ingredients of a sample gas, comprising:
   a sample gas-introducing passage;
   a sample gas flow-dividing and gas-diluting means connected to said gas-introducing passage for dividing the sample gas into a plurality of gas flow in a desired flow-dividing ratio, and simultaneously diluting the plurality of divided sample gas flows, said means having a plurality of parallel connected flow-dividing ratio/dilution ratio setting devices; each of said ratio setting devices having a plurality of parallel connected flow rate limiting elements, and having an inlet manifold providing a space from which said limiting elements extend with the openings into the inlet elements side by side, the outlets from said limiting elements being connected in an outlet manifold, and a valve means movable in said inlet manifold and selectively positionable between individual pairs of element inlet openings and dividing said inlet manifold space into two non-communicating parts, thereby causing the openings on one side of said valve means to open into one part of the inlet manifold space and the openings on the other side of said valve means to open into the other part of said inlet manifold space, said sample gas-introducing passage being connected to one part of said inlet maifold space, and dilution gas supply means connected to the other part of said inlet manifold space; and
   a plurality of gas concentration detectors, one for the gas flow from each of said ratio setting devices, and connected, in parallel with each other, to their respective outlet manifolds for receiving the respective diluted gas flows from said outlet manifolds of each of said flow-dividing ratio/dilution ratio setting devices.

* * * * *